United States Patent [19]

North et al.

[11] Patent Number: 5,633,276

[45] Date of Patent: May 27, 1997

[54] INDOLINE DERIVATIVES, METHOD OF PREPARATION AND USE

[75] Inventors: Peter C. North; Malcolm C. Carter, both of Stevenage, United Kingdom

[73] Assignee: Glaxo Group Limited, London, England

[21] Appl. No.: 652,460

[22] PCT Filed: Dec. 20, 1994

[86] PCT No.: PCT/EP94/04220

§ 371 Date: Jun. 14, 1996

§ 102(e) Date: Jun. 14, 1996

[87] PCT Pub. No.: WO95/17405

PCT Pub. Date: Jun. 29, 1995

[30] Foreign Application Priority Data

Dec. 22, 1993 [GB] United Kingdom ............. 9326192

[51] Int. Cl.⁶ .................. A61K 31/40; C07D 491/048
[52] U.S. Cl. .................................. 514/411; 548/430
[58] Field of Search ........................ 548/430; 514/411

[56] References Cited

U.S. PATENT DOCUMENTS

| 4,680,411 | 7/1987 | Picart ............................ 548/430 |
| 4,738,972 | 4/1988 | Eggler et al. .................. 514/314 |

FOREIGN PATENT DOCUMENTS 0043752   1/1982   European Pat. Off. .
0207605   1/1987   European Pat. Off. .

OTHER PUBLICATIONS

Kim et al., *Canadian Journal of Chemistry*, vol. 60, No. 16, 1982, 2093–2098.

Primary Examiner—Fiona T. Powers
Attorney, Agent, or Firm—Bacon & Thomas

[57] ABSTRACT

A compound of formula (I)

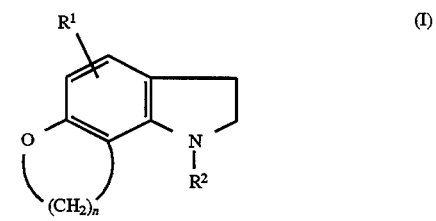

wherein, $R^1$ is hydrogen, halogen or $C_{1-6}$ alkyl;
$R^2$ is a group of formula $-CR^3R^4(CH_2)_pNR^5COR^6$;
$R^3$, $R^4$ and $R^5$, which may be the same or different, are hydrogen or $C_{1-6}$ alkyl;
$R^6$ is $C_{1-6}$ alkyl or $C_{3-7}$ cycloalkyl;
n is an integer of 2, 3 or 4;
p is an integer of 1, 2, 3 or 4;
and pharmaceutically acceptable salts and solvates thereof.
A compound of formula (I) is useful in the treatment of conditions associated with a disturbed functioning of the melatonin system.

17 Claims, No Drawings

INDOLINE DERIVATIVES, METHOD OF PREPARATION AND USE

This application is a 371 of PCT/EP 94/04,220 filed Dec. 20, 1994, published as WO95/17405, Jun. 29, 1995.

This invention relates to tricyclic indoline derivatives, to processes for their preparation, to pharmaceutical compositions containing them and to their medical use.

The invention thus provides compounds of formula (I)

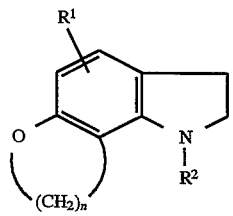

wherein $R^1$ is hydrogen, halogen or $C_{1-6}$ alkyl;

$R^2$ is a group of formula $-CR^3R^4(CH_2)_pNR^5COR^6$;

$R^3$, $R^4$ and $R^5$, which may be the same or different, are hydrogen or $C_{1-6}$ alkyl;

$R^6$ is $C_{1-6}$ alkyl or $C_{3-7}$ cycloalkyl;

n is an integer of 2, 3 or 4;

p is an integer of 1, 2, 3 or 4;

and pharmaceutically acceptable salts and solvates (e.g. hydrates) thereof.

It will be appreciated that in formula (I) hereinabove the substituent $R^1$ may be attached at either available position on the phenyl portion of the tricylic ring.

As used herein, an alkyl group may be a straight chain or branched chain alkyl group. Examples of suitable alkyl groups include $C_{1-4}$ alkyl groups, for example methyl, ethyl and isopropyl groups. A preferred alkyl group is methyl.

A halogen substituent may be, for example, fluorine, chlorine, bromine or iodine.

$R^2$ preferably represents a group $-CR^3R^4(CH_2)_pNHCOR^6$ wherein $R^3$ and $R^4$ each independently represent hydrogen or $C_{1-3}$ alkyl (e.g. methyl), p is an integer of 1 or 2, especially 1, and $R^6$ is $C_{1-3}$ alkyl (e.g. methyl) or $C_{3-5}$ cycloalkyl (e.g. cyclopropyl or cyclobutyl).

Examples of the group $R^1$ include hydrogen, halogen (e.g. chlorine) and $C_{1-3}$ alkyl (e.g. methyl).

A preferred group of compounds of the invention are compounds of formula (Ia)

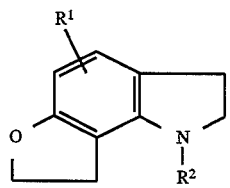

and pharmaceutically acceptable salts and solvates (e.g. hydrates) thereof, wherein $R^1$ and $R^2$ are as defined hereinabove.

It is to be understood that the present invention covers all combinations of particular and preferred groups described hereinabove.

Particular compounds according to the present invention include:

N-[2-(2,3,8,9-Tetrahydro-7H-pyrano[2,3-g]indol-1-yl)-ethyl]-acetamide;

N-[2-(2,3,7,8-Tetrahydro-1H-furo[2,3-g]indol-1-yl)-ethyl]-acetamide;

N-[2-(5-Chloro-2,3,7,8-tetrahydro-1H-furo[2,3-g]indol-1-yl)-ethyl]-acetamide;

Cyclopropanecarboxylic acid [2-(2,3,7,8-tetrahydro-1H-furo[2,3-g]indol-1-yl)-ethyl]-amide;

and pharmaceutically acceptable salts and solvates thereof.

A particularly suitable compound according to the present invention is N-[2-(2,3,7,8-Tetrahydro-1H-furo[2,3-g]indol-1-yl)-ethyl]-acetamide, and pharmaceutically acceptable salts and solvates thereof.

Pharmaceutically acceptable salts of the compounds of formula (I) include those derived from pharmaceutically acceptable inorganic and organic acids. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids. A particularly suitable pharmaceutically acceptable salt of the compounds of formula (I) is the hydrochloride salt. Other acids such as oxalic, while not, in themselves pharmaceutically acceptable, may be useful as intermediates in obtaining the compounds of the invention and their pharmaceutically acceptable acid addition salts.

References hereinafter to a compound of formula (I) includes the compound and its pharmaceutically acceptable salts.

The compounds of formula (I) may contain at least one asymmetric carbon atom and may exist as stereoisomers. The compounds of formula (I) thus include the d- and l-isomers and mixtures, for example racemic mixtures, thereof.

The compounds of formula (I) are of use in the treatment of disorders which arise from a disturbed functioning of the melatonin system. In particular the compounds of formula (I) may be used in the treatment of chronobiological disorders, especially in the elderly population, glaucoma, cancer, psychiatric disorders, osteoporosis, neurodegenerative diseases or neuroendocrine disorders arising as a result of or influenced by the melatonin system.

Chronobiological disorders include seasonal affective disorders (SAD), primary and secondary insomnia disorders, primary and secondary hypersomnia disorders, sleep-wake schedule disorders (including advanced phase type, delayed phase type, disorganised type and frequently-changing type) and other dyssomnias, especially those caused by ageing, dementias, blindness shift work and by rapid time-zone travel, commonly known as jet lag.

Cancers which may be treated with a compound of formula (I) include solid tumours, e.g. melanomas and breast carcinomas.

Psychiatric disorders which may be related to altered melatonin function or influenced by melatonin and circadian rhythms include mood disorders (including bipolar disorders of all types, major depression, dysthymia and other depressive disorders), psychoactive substance dependence and abuse, anxiety disorders (including panic disorder, agoraphobia, social phobia, simple phobia, obsessive-compulsive disorder, post-traumatic stress disorder and generalised anxiety disorder), schizophrenia, epilepsy and epileptic seizures (including grand mal, petit real, myoclonic epilepsy and partial seizures), disorders of involuntary movement (including those due to Parkinson's disease, and drug-induced involuntary movements) and dementias (including primary degenerative dementia of the Alzheimer type).

Neurodegenerative diseases which may be related to altered melatonin function or influenced by melatonin and biological rhythms include multiple sclerosis and stroke.

Neuroendocrine disorders which may be related to altered melatonin function or influenced by melatonin and biological rhythms include peptic ulceration, emesis, psoriasis, benign prostatic hyperplasia, hair condition and body weight. Particular neuroendocrine disorders which may be treated include those relating to the regulation of reproductive maturation and function include idiopathic delayed puberty, sudden infant death, premature labour, infertility, antifertility, premenstrual syndrome (including late luteal phase dysphoric disorder) and sexual dysfunction (including sexual desire disorders, male erectile disorder, postmenopausal disorders and orgasm disorders). The compounds may also be used to manipulate breeding cycles, body weight, coat colour and oviposition of susceptible hosts, including birds, insects and mammals. The compounds of formula (I) may also have sedative, anti-inflammatory and analgesic effects, effects on the microcirculation and immunomodulant effects and may be useful for the treatment of hypertension, migraine, cluster headache, arthritis, regulation of appetite and in the treatment of eating disorders such as obesity, anorexia nervosa and bulimia nervosa.

There is thus provided in a further aspect of the invention a compound of formula (I) for use in therapy, in particular in human medicine. It will be appreciated that use in therapy embraces but is not necessarily limited to use of a compound of formula (I) as an active therapeutic substance.

There is also provided as another aspect of the invention a compound of formula (I) for use in the preparation of a medicament for use in the treatment of conditions associated with a disturbed functioning of the melatonin system.

In an alternative or further aspect of the invention there is provided a method for the treatment of a mammal, including man, comprising administration of an effective amount of a compound of formula (I), in particular for the treatment of conditions associated with a disturbed functioning of the melatonin system.

It will be appreciated by those skilled in the art that reference herein to therapy and treatment extends to prophylaxis as well as the treatment of established symptoms.

While it is possible that, for use in therapy, a compound of formula (I) may be administered as the raw chemical it is preferable to present the active ingredient as a pharmaceutical formulation.

The invention thus further provides a pharmaceutical formulation comprising a compound of formula (I) together with one or more pharmaceutically acceptable carriers therefor. The carrier(s) must be 'acceptable' in the sense of being compatible with the other ingredients of the formulation and not deleterious to the recipient thereof.

There is further provided by the present invention a process of preparing a pharmaceutical formulation, which process comprises mixing a compound of formula (I) with one or more pharmaceutically acceptable carriers therefor.

Pharmaceutical formulations include those suitable for oral, rectal, vaginal, nasal, topical or parenteral (including intramuscular, subcutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl-p-hydroxybenzoates or sorbic acid).

For topical administration in the mouth, the compositions may take the form of buccal or sub-lingual tablets, drops or lozenges formulated in conventional manner.

For topical administration to the epidermis the compounds may be formulated as creams, gels, ointments or lotions or as a transdermal patch. Such compositions may for example be formulated with an aqueous or oily base with the addition of suitable thickening, gelling, emulsifying, stabilising, dispersing, suspending and/or colouring agents.

The compounds of the invention may be formulated for parenteral administration by injection, conveniently intravenous, intramuscular or subcutaneous injection, for example by bolus injection or continuous intravenous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glyceride.

Pessaries for vaginal administration may be formulated in a similar manner.

For intranasal administration the compounds of the invention may be used, for example, as a liquid spray, as a powder or in the form of drops.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

Any of the pharmaceutical compositions described above may be presented in a conventional manner associated with controlled release forms.

The active ingredient may conveniently be presented in unit dose form. A convenient unit dose formulation contains the active ingredient in an amount of from about 0.01 mg to about 200 mg.

It will be appreciated that the precise dose administered will depend on the age and condition of the patient, the particular compound used and the frequency and route of administration and will ultimately be at the discretion of the attendant physician. The compound may be administered in single or divided doses and may be administered one or more times, for example 1 to 4 times per day.

A proposed dose of the compounds of the invention for oral, rectal, vaginal, intranasal, topical or parenteral administration to man (of approximately 70 kg bodyweight) for the treatment of conditions associated with a disturbed functioning of the melatonin system is 0.01 to 200 mg of the active ingredient per unit dose which could be administered, for example, 1 to 4 times per day.

For oral administration a unit dose will preferably contain from 0.1 to 200 mg of the active ingredient. A unit dose for parenteral administration will preferably contain 0.1 to 5 mg of the active ingredient.

Aerosol formulations are preferably arranged so that each metered dose or 'puff' delivered from a pressurised aerosol contains 0.2 mg to 2 mg of a compound of the invention, and capsules and cartridges delivered from an insufflator or an inhaler, contain 0.2 mg to 20 mg of a compound of the invention. The overall daily dose by inhalation with an aerosol will be within the range 1 mg to 100 mg. Administration may be several times daily, for example from 2 to 8 times, giving for example 1, 2 or 3 doses each time.

Dosages of the compounds of the invention for rectal, vaginal, intranasal or topical administration are similar to those for oral administration.

The compounds of the invention may, if desired, be administered in combination with one or more other therapeutic agents such as a hypnotic or antidepressant agent, or an anti-cancer agent such as tamoxiphen, or in combination with radiation therapy to treat cancer.

The combinations referred to above may conveniently be presented for use in the form of a pharmaceutical formulation and thus pharmaceutical formulations comprising a compound of formula (I) together with at least one other therapeutic agent and one or more pharmaceutically acceptable carriers therefor comprise a further aspect of the invention.

When compounds of formula (I) are used in combination with other therapeutic agents, the compounds may be administered either sequentially or simultaneously by any convenient route.

When such combinations are employed the dose of each component of the combination will in general be that employed for each component when used alone.

Compounds of formula (I) and pharmaceutically acceptable salts and solvates (e.g. hydrates) thereof, may be prepared by methods known in the art for the preparation of analogous compounds. In particular the compounds of formula (I) may be prepared by the methods outlined below and which form a further aspect of the invention. In the following processes, $R^1$, $R^3$, $R^4$, $R^5$, n and p are as defined for formula (I).

According to one general process (A) a compound of formula (I) may be prepared by acylation of a compound of formula (II)

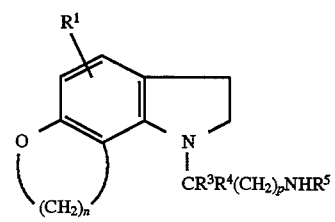

Suitable acylating agents which may conveniently be used in the above process include acid anhydrides and acid halides. The reaction is conveniently effected in a suitable solvent such as an ether (e.g. diethyl ether, tetrahydrofuran or dioxan), a hydrocarbon such as toluene or a halogenated hydrocarbon (e.g. dichloromethane), preferably in the presence of a base such as pyridine or a tertiary amine (e.g. diisopropylethylamine), at a temperature in the range of 0° to 100° C., preferably 0° to 20° C.

Compounds of formula (II) in which $R^5$ is hydrogen may conveniently be prepared by the reduction of compounds of formula (III)

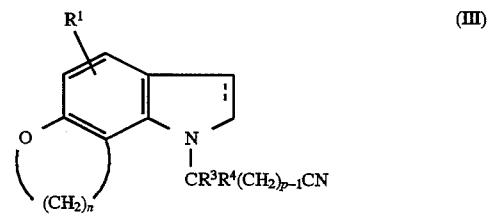

(wherein the dotted line indicates an optional double bond). The reduction may conveniently be effected using a boron hydride reducing agent such as borane-tetrahydrofuran complex in an ether solvent (e.g. tetrahydrofuran) optionally in the presence of a suitable acid (e.g. trifluoroacetic acid, hydrochloric acid or the like) at a suitable temperature, for example from 0° to 100° C. Alternatively, the reduction may employ catalytic hydrogenation in the presence of a noble metal catalyst, such as platinum, palladium or the like, in a suitable organic solvent, such as an alcoholic solvent, e.g. ethanol, conveniently at a temperature in the range of 0° to 100° C., aptly at room temperature.

Compounds of formula (II) in which $R^5$ is $C_{1-6}$ alkyl may be prepared by N-alkylation of compounds of formula (II) in which $R^5$ is hydrogen using standard procedures.

Compounds of formula (III) may conveniently be prepared by alkylating compounds of formula (IV)

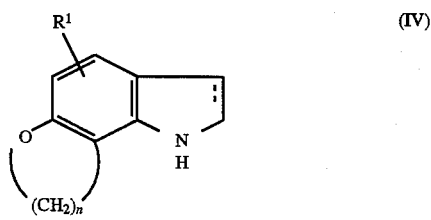

using an agent $HalCR^3R^4(CH_2)_{p-1}CN$ in which Hal is a halogen atom (fluorine, bromine, chlorine or iodine), suitably in the presence of a base. The alkylation may be carried out under standard conditions. For example, the reaction may be effected in a ketonic solvent in the presence of an alkali or alkaline earth metal carbonate (e.g. potassium carbonate) at an elevated temperature (e.g. under reflux). Alternatively, the reaction may be effected in dimethylformamide in the presence of an alkali metal hydride (e.g. sodium hydride) at about ambient temperature.

Compounds of formula (IV) in which the dotted line indicates a double bond may be prepared by the decarboxylation of compounds of formula (V)

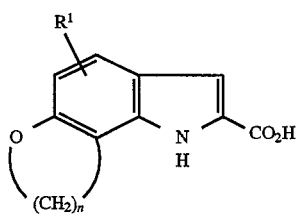

Thus, compounds of formula (V) may be decarboxylated by heating the compounds at a very high temperature (e.g. at about 250° C.), optionally in the presence of copper and a suitable copper salt, such as copper (I) oxide, cuprous oxide and the like.

Compounds of formula (IV) in which the dotted line indicates a double bond may be converted to the corresponding saturated analogues of formula (IV) by reduction, for example using the conditions described above to prepare the compounds of formula (II) from compounds of formula (III).

Compounds of formula (V) may be prepared by the cyclisation and deesterification of compounds of formula (VI)

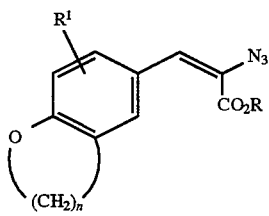

(wherein R is a $C_{1-6}$ alkyl group, e.g. methyl). The cyclisation reaction may conveniently be effected by heating (VI) to reflux in an aromatic hydrocarbon solvent (e.g. xylene). Conversion of the so-formed ester to the corresponding acid of formula (V) involves routine hydrolysis, for example using a base such as a hydroxide (e.g. sodium hydroxide) at an elevated temperature (e.g. under reflux).

Compounds of formula (VI) may be prepared by treating compounds of formula (VII)

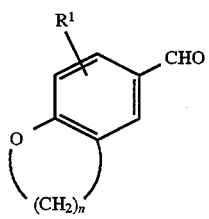

with an alkyl azidoacetate in the presence of a strong base (e.g. potassium tert-butoxide) at a temperature of from −20° to +10° C.

Compounds of formula (VII) are either known compounds described, for example, in WO 86/07056 or may be prepared by methods analogous to those described therein.

Alternatively compounds of formula (IV) in which the dotted line indicates a double bond may be prepared by cyclisation of compounds of formula (VIII)

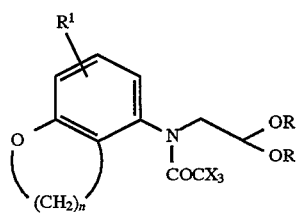

wherein X represents a halogen atom (e.g. fluorine) and R is a $C_{1-6}$ alkyl group, such as methyl or ethyl. Preparation of compounds of formula (IV) typically involves addition of a solution of compounds of formula (VIII) (suitably in a chlorinated organic solvent such as dichloromethane, dichloroethane or the like) to an acidic medium, such as halogenated acetic acid and/or acetic anhydride optionally in a chlorinated organic solvent as described above. Suitably the addition is carried out at 0° C. under an inert atmosphere such as nitrogen. The reaction may be progressed by allowing the reagents to reach room temperature, and stirring for about 18 to 20 hours. The resulting mixture is generally treated with a base, such as an alkali metal hydroxide, prior to extraction of desired compounds of formula (IV).

Compounds of formula (VIII) are suitably prepared by acylation of compounds of formula (IX)

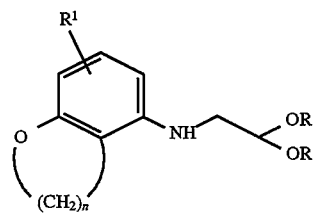

employing suitable acylating agents such as acid anhydrides and acid halides. Suitably a halogenated acetic arthydride (aptly trifluoroacetic arthydride) in a chlorinated organic solvent as described above is added to a solution of a compound of formula (IX) in a basic solvent, such as triethylamine and the like. Generally the addition is carried out at 0° C. under an inert atmosphere such as nitrogen.

Preparation of compounds of formula (IX) suitably employs known starting materials of formula (X) shown below, which starting materials can be prepared according to *J. Heterocyclic Chem.*, (1973), Vol 10(4), page 623, Compounds of formula (X)

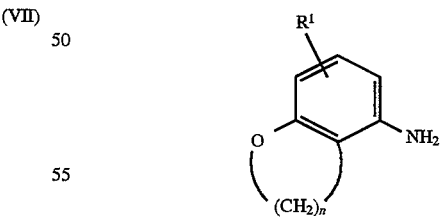

are aptly reacted with a suitable acetal derivative, conveniently in the presence of a base (an alkali metal carbonate being an example of an appropriate base), with heating over a prolonged period of time (such as 40 to 65 hours) at an elevated temperature in the range of 90° to 110° C., in order to yield compounds of formula (IX).

Compounds of formula (I) in which $R^1$ represents halogen may be prepared via compounds of formulae (II), (III) and (IV) wherein $R^1$ represents halogen employing process steps substantially as hereinbefore described. Suitably compounds of formula (IV) in which $R^1$ represents halogen are prepared from compounds of formula (XI) wherein $R^1$ represents halogen and the dotted line indicates an optional double bond.

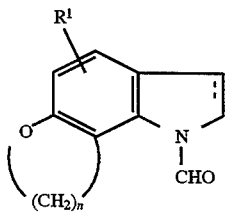

(XI)

Aptly a compound of formula (XI) is dissolved in an organic solvent, such as an alcoholic solvent, acidified, and the mixture subjected to stirring and refluxing for a suitable length of time to yield a corresponding compound of formula (IV).

Conveniently a compound of formula (XI) wherein $R^1$ represents halogen as described above is prepared from a corresponding compound of formula (XI) wherein $R^1$ represents hydrogen by halogenation employing suitable halogenating agents and techniques.

Suitably compounds of formula (XI) wherein $R^1$ represents hydrogen as described above may be prepared from compounds of formula (IV) wherein $R^1$ represents hydrogen by reaction of the latter with an appropriate anhydride in an acidic medium.

According to a further embodiment of the present invention, there is provided a further general process (B) wherein a compound of formula (I) may be prepared from a compound of formula (XII)

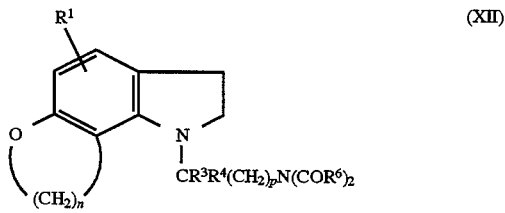

(XII)

suitably by stirring for several hours (17 to 19 hours) in a basic medium, conveniently an alkali metal hydroxide or the like, under an inert atmosphere such as nitrogen, followed by refluxing for 1 to 2 hours.

Aptly a compound of formula (XII) may be prepared by acylation of a compound of formula (II) employing acylation techniques substantially as hereinbefore described.

According to a yet further embodiment of the present invention, there is provided a general process (C) whereby a compound of formula (I) may be prepared by alkylating a saturated compound of formula (IV). Suitably alkylation is achieved by refluxing a compound of formula (IV) together with an alkylating agent over several days. Suitable alkylating agents include $HalCR^3R^4(CH_2)_pNR^5COR^6$ (wherein Hal, $R^3$, $R^4$, $R^5$, $R^6$ and p are as hereinbefore defined), $ANR^5COR^6$ wherein A represents a 2-membered alkyl chain or the like.

Compounds of formulae (II)–(IX), (XI) and (XII) are novel intermediates and represent further individual aspects of the present invention. Compounds of formula (IVa) represent a further particular aspect of the invention.

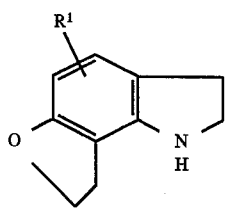

(IVa)

According to another general process (D), a compound of formula (I) may be prepared by subjecting a protected derivative of a compound of formula (I) or a salt thereof to reaction to remove the protecting group or groups.

Thus, according to a further aspect of the invention, the following reactions may according to process (D), if desirable and/or if necessary, be carried out in any appropriate sequence:

(i) removal of any protecting groups; and (ii) conversion of a compound of formula (I) or a salt thereof into a pharmaceutically acceptable salt thereof.

Thus, at an earlier stage in the preparation of a compound of formula (I) it may have been necessary and/or desirable to protect one or more sensitive groups in the molecule to prevent undesirable side reactions.

The protecting groups used in the preparation of compounds of formula (I) may be used in conventional manner. See for example 'Protective Groups in Organic Chemistry' Ed. J. F. W. McOmie (Plenum Press 1973) or 'Protective Groups in Organic Synthesis' by Theodora W Greene (John Wiley and Sons 1991).

According to another general process (E), compounds of formula (I) may be prepared from other compounds of formula (I) by interconversion reactions. In particular, acid addition salts of compounds of formula (I) may be prepared from a corresponding compound of formula (I) by suitable acid treatment, for example addition of a suitable acid, such as hydrochloric acid, generaly in the presence of an organic solvent such as an alcohol or ester. Aptly the reagents may be stirred at room temperature for a convenient length of time. Alternatively, an acid may be added dropwise to a solution of a compound of formula (I) in an appropriate organic solvent as described above, optionally under an inert atmosphere such as nitrogen.

Where it is desired to isolate a compound of the invention as a salt, for example as an acid addition salt, this may be achieved by treating the free base of general formula (I) with an appropriate acid, preferably with an equivalent amount, or with creatinine sulphate in a suitable solvent (e.g. ethanol).

Compounds of the invention may be isolated in association with solvent molecules by crystallisation from or evaporation of an appropriate solvent.

Individual enantiomers of the compounds of the invention may be prepared from racemates by resolution using methods known in the art for the separation of racemic mixtures into their constituent enantiomers, for example using chiral HPLC.

As well as being employed as the last main step in the preparative sequence, the general methods indicated above for the preparation of the compounds of the invention may also be used for the introduction of the desired groups at an intermediate stage in the preparation of the required compound. It should therefore be appreciated that in such multi-stage processes, the sequence of reactions should be chosen in order that the reaction conditions do not affect groups present in the molecule which are desired in the final product.

The invention is further illustrated by the following Examples which should not be construed as constituting a limitation thereto. All temperatures are in ° C. THF means tetrahydrofuran. EtOH means ethanol. EtOAc means ethyl acetate. DMF means dimethylformamide. $NH_3$ means commercially available aqueous ammonium hydroxide. TFA means trifluoroacetic acid. TFAA means trifluoroacetic anhydride. Dried means dried over anhydrous sodium sulphate (unless otherwise stated). Chromatography was performed on silica (Merck 9385 unless otherwise stated). System A is dichloromethane/ethanol/aqueous ammonia. T.l.c. means thin layer chromatography on silica gel. The n.m.r. analysis was conducted at 250 mHz.

INTERMEDIATE 1

2-Azido-3-(2,3-dihydro-benzofuran-5-yl)-acrylic acid methyl ester

To a cold (−10° C.) stirred solution of potassium tert-butoxide (6.06 g) in dry methanol (40 ml) was added dropwise a mixture of 2,3-dihydrobenzofuran-5-carboxaldehyde (2 g) and methyl azidoacetate (6.21 g). The mixture was stirred for 1 h at −10° C. and then stored at 0° C. for 18 h. The resulting pale yellow microcrystals were collected by filtration to give the title compound (3.12 g), m.p. 77°–80° C.

INTERMEDIATE 2

7,8-Dihydro-1H-furo[2,3-g]indole-2-carboxylic acid

A solution of Intermediate 1 (3.1 g) in xylene (350 ml) was heated to reflux for 2 h. The cooled mixture was washed with water (100 ml) and then the aqueous layer extracted with xylene (50 ml). The combined organic phases were dried and evaporated, and the residue dissolved in ethanol (40 ml). 2N Sodium hydroxide was added (20 ml) and the mixture heated to reflux for 2 h. The ethanol was evaporated and the mixture extracted with ether (2×50 ml). The aqueous layer was then acidified and extracted with EtOAc (2×75 ml). The dried extracts were evaporated to give the title compound as a yellow/orange solid (878 mg), m.p. 160° C. (chars) 213° C. (dec.).

INTERMEDIATE 3

7,8-Dihydro-1H-furo[2,3-g]indole

Intermediate 2 (875 mg) was placed in a pre-heated Woods metal bath (ca. 250° C.) for 2 min until $CO_2$ evolution had ceased. The material was pre-absorbed onto silica gel and then chromatographed (35 g). Elution with EtOAc:cyclohexane (1:4) gave the title compound as a beige solid (232 mg). $^1H$ n.m.r.($CDCl_3$)7.82δ (1$\underline{H}$,br s), 7.4δ (1 $\underline{H}$,d), 7.09δ (1$\underline{H}$,m), 6.73δ (1$\underline{H}$,d), 6.52δ (1$\underline{H}$,m), 4.67δ (2 $\underline{H}$,t), 3.32δ (2$\underline{H}$,t).

INTERMEDIATE 4

2,3,7,8-Tetrahydro-1H-furo[2,3-g]indole

Intermediate 3 (275 mg) was dissolved in borane THF complex (1M solution, 2.6 ml) and was stirred at 0° C. under $N_2$, then trifluoroacetic acid (2.6 ml) was added dropwise. Stirring was maintained at 0° C. for 45 min and saturated potassium carbonate solution added. The mixture was extracted with EtOAc (2×30 ml). The dried extracts were evaporated and the residue chromatographed on silica gel (30 g). Elution with EtOAc:cyclohexane (1:2) gave the title compound as a pale brown oil, which solidified (215 mg), m.p. 48°–50° C.

T.l.c. EtOAc:cyclohexane (1:2) Rf 0.25.

INTERMEDIATE 5

(2,3,7,8-Tetrahydro-1H-furo[2,3-g]indol-1-yl) acetonitrile

A mixture of Intermediate 4 (122 mg), iodoacetonitrile (0.06 ml) and potassium carbonate (105 mg) in methyl isobutyl ketone (5 ml) was heated to reflux, under $N_2$, for 18 h. The cooled mixture was partitioned between 2N $Na_2CO_3$ (20 ml) and EtOAc (2×30 ml). The dried extracts were evaporated and the residue chromatographed on silica gel (35 g). Elution with EtOAc:cyclohexane (1:3) gave the title compound as a beige solid (123 mg), m.p. 122°–4° C. T.l.c. EtOAc:cyclohexane (1:2) Rf 0.37.

INTERMEDIATE 6

(7,8-Dihydro-1H-furo[2,3-g]indol-1-yl)acetonitrile

To a stirred solution of Intermediate 3 (227 mg) in dry DMF (8 ml), was added sodium hydride (60% in oil, 85 mg). The mixture was stirred for 0.5 h and then chloroacetonitrile (0.13 ml) was added dropwise. The mixture was then left to stand at 20° C. for 2 days and was then partitioned between 2N $Na_2CO_3$ solution (60 ml) and EtOAc (2×70 ml). The dried extracts were evaporated and the residue chromatographed on silica gel (40 g). Elution with EtOAc:cyclohexane (1:3) gave the title compound as an off-white solid (109 mg).

$^1H$ n.m.r.($CDCl_3$) 7.38δ (1$\underline{H}$,d), 6.9δ (1$\underline{H}$,d), 6.77δ (1 $\underline{H}$,d), 6.53δ (1$\underline{H}$,d), 5.04δ (2$\underline{H}$,s), 4.70δ (2$\underline{H}$,t), 3.65 (2 $\underline{H}$,t).

INTERMEDIATE 7

2-(2,3,7,8-Tetrahydro-1H-furo[2,3-g]indol-1-yl) ethylamine (a) A solution of Intermediate 6 (160 mg) in dry THF (5 ml) was treated with borane THF complex (1M in THF, 8 ml) and was stirred, under $N_2$, at 20° C. for 18 h. The mixture was then cooled (0° C.) and trifluoroacetic acid (5 ml) added. After a further 30 min saturated potassium carbonate solution was added, dropwise initially, and then the mixture was extracted with EtOAc (2×40 ml). The dried extracts were evaporated and chromatographed on silica gel (20 g). Elution with System A (100:8:1) gave the title compound as a pale brown semi-solid (80 mg).

$^1H$ n.m.r.($CDCl_3$) 6.82δ (1$\underline{H}$,d), 6.18δ (1$\underline{H}$,d), 4.52δ (2 $\underline{H}$,t), 3.37δ (2$\underline{H}$,t), 3.32–3.2 δ(4$\underline{H}$,2xt), 2.97–2.87δ (4 $\underline{H}$,2xt), 1.8δ (2$\underline{H}$,br s).

(b) To a stirred, refluxing, solution of Intermediate 5 (203 mg) in dry THF (10 ml) was added dropwise borane THF complex (1M solution, 3 ml). Heating was maintained for 5 h and then the mixture was cooled, and methanol (3 ml) added, cautiously at first. 2N HCl (3 ml) was then added, and the mixture heated to reflux for a further 1 h. The cooled mixture was then partitioned between saturated $K_2CO_3$ (40 ml) and EtOAc (2×35 ml). The dried extracts were evaporated and the residue chromatographed on silica gel (25 g). Elution with System A (100:8:1) gave the title compound as a pale yellow oil which solidified (166 mg). The n.m.r. data for this solid was consistent with that for the same compound prepared in part (a) above.

INTERMEDIATE 8

Chroman-5-yl-(2,2-diethoxy-ethyl)-amine

Bromoacetaldehyde diethyl acetal (11.8 ml) was added to a mixture of chroman-5-yl-amine (5.85 g) (prepared according to *J. Heterocyclic Chem.*, (1973), Vol 10 (4) page 623), and potassium carbonate (10.84 g) in dry DMF (70 ml) at room temperature under $N_2$. The mixture was heated at 100° C. for 60 h. The cooled mixture was partitioned between water (800 ml) and ether (3×200 ml). The combined organic extracts were washed with brine/water 1:1 (2×200 ml) and dried. The solvent was evaporated and the residue purified by flash column chromatography on silica. Elution with cyclohexane/ethyl acetate 6:1 gave the title compound as a pale yellow oil (8.0 g).

T.l.c. $SiO_2$ cyclohexane/ethyl acetate 6:1, Rf 0.35.

INTERMEDIATE 9

N-Chroman-5-yl-N-2,2-diethoxy-ethyl)-2,2,2-trifluoro-acetamide

Trifluoroacetic anhydride (4.67 ml) in dry dichloromethane (10 ml) was added dropwise to a solution of Intermediate 8 (7.99 g) and triethylamine (4.62 ml) in dry dichloromethane (190 ml) at 0° C. under $N_2$. The mixture was allowed to warm to room temperature and stirred for 2 h. The mixture was washed with water (2×100 ml) and dried. The solvent was evaporated to give the title compound as a pale yellow oil (10.35 g).

T.l.c. cyclohexane/ethyl acetate (6:1), Rf 0.6

INTERMEDIATE 10

1,7,8,9-Tetrahydro-pyrano[2,3-g]indole

A solution of Intermediate 9 (0.1 g) in dry dichloromethane (1 ml) was added dropwise to a solution of TFA (1.5 ml) and TFAA (1.0 ml) in dry dichloromethane (10 ml) at 0° C. under $N_2$. The mixture was allowed to warm to room temperature and stirred for 20 h. The solution was cooled and basified to $pH_{12}$ with 5% potassium hydroxide in methanol. The mixture was stirred for 5 min, then evaporated. The residue was partitioned between water (15 ml) and ethyl acetate (3×10 ml). The combined organic extracts were washed with brine (1×20 ml) and dried. The solvent was evaporated and the residue purified by flash chromatography on silica. Elution with cyclohexane/ethyl acetate 10:1 gave the title compound as a colourless solid (21.7 mg).

T.l.c. cyclohexane/ethyl acetate (4:1), Rf 0.35.

INTERMEDIATE 11

1,2,3,7,8,9-Hexahydro-pyrano[2,3-g]indole

Borane (1.0M in THF; 5 ml) was added dropwise to a solution of Intermediate 10 (434 mg) in dry THF (10 ml) at 0° C. under $N_2$. Trifluoroacetic acid (32 ml) was then added dropwise and the mixture stirred for 10 min at 0° C. 2N sodium hydroxide (8 ml) was added dropwise cautiously at 0° C. to pH12. The mixture was then partitioned between water (15 ml) and ethyl acetate (3×15 ml). The combined organic extracts were washed with brine (1×20 ml) and dried. The solvent was evaporated and the mixture was purified by flash column chromatography on silica. Elution with cyclohexane/ethyl acetate 4:1 gave the title compound as a colourless gum (222 mg). T.l.c. Ethyl acetate/cyclohexane (4:1), Rf 0.3.

INTERMEDIATE 12

(2,3,8,9-Tetrahydro-7H-pyrano[2,3-g]indol-1yl)-acetonitrile

Iodoacetonitrile (0.11 ml) was added to a mixture of Intermediate 11 (222 mg) and potassium carbonate (210 mg) in MIBK (10 ml) at room temperature. The mixture was heated under reflux for 5 h, cooled to room temperature, then partitioned between water (15 ml) and ethyl acetate (3×15 ml). The combined organic extracts were washed with brine (1×20 ml) and dried ($MgSO_4$). The solvent was evaporated and the residue purified by flash column chromatography on silica. Elution with cyclohexane/ethyl acetate 5:1 gave the title compound as a colourless gum which crystallised on standing (0.25 g). T.l.c. cyclohexane/ethyl acetate (3:1), Rf 0.37.

INTERMEDIATE 13

2-(2,3,8,9-Tetrahydro-7H-pyrano[2,3-g]indol-1-yl)-ethylamine

Borane (1.0M; 2.27 ml) was added dropwise to a solution of Intermediate 12 (243 mg) in dry THF (5 ml) at 0° C. under $N_2$. The solution was heated under reflux for 3 h, cooled to 0° C. and methanol (1 ml) was added cautiously dropwise until effervessing ceased. 2N HCl (2 ml) was added (to pH1) and the mixture heated under reflux for 15 min, cooled to 0° C. and basified to pH12 with 2N NaOH (3 ml). The mixture was partitioned between water (10 ml) and ethyl acetate (3×15 ml). The combined organic extracts were washed with brine (1×15ml) and dried. The solvent was evaporated and the residue purified by flash column chromatography on silica. Elution with dichloromethane/ethanol/ammonia 100:8:1 gave the title compound as a colourless gum (160 mg).

T.l.c. Dichloromethane/ethanol/ammonia (100:8:1 ), Rf 0.3.

INTERMEDIATE 14

2,3,7,8-Tetrahydro-1H-furo[2,3-g]indole-1-carbaldehyde

To a stirred solution of Intermediate 4 (320 mg) in formic acid (3 ml) was added dropwise acetic anhydride (1 ml). The mixture was then heated to ca. 60° C. for 20 min. The mixture was then added cautiously to 2N $Na_2CO_3$, and was extracted into EtOAc. Evaporation of the dried extract gave an off-white solid (360 mg).

T.l.c. ($SiO_2$) $CH_2Cl_2$:EtOH:$NH_3$; 400:8:1, Rf 0.29

INTERMEDIATE 15

5-Chloro-2,3,7,8-tetrahydro-1H-furo[2,3-g]indole-1-carbaldehyde

A stirred solution of Intermediate 14 (180 mg) in glacial acetic acid (4 ml) was treated with N-chlorosuccinimide (140 mg) and was stirred for 7 h. The mixture was partitioned between 2N $Na_2CO_3$ and EtOAc. Evaporation of the dried extracts gave a grey solid (218 mg).

T.l.c. ($SiO_2$) EtOAc:cyclohexane; 1:1, Rf 0.19

INTERMEDIATE 16

5-Chloro-2,3,7,8-tetrahydro-1H-furo[2,3-g]indole

Intermediate 15 (210 mg) was dissolved in methanol (5 ml) and 2N HCl (1 ml) added. The mixture was stirred at 20° C. for 18 h, then at reflux for 1 h. The mixture was allowed to cool, and the methanol evaporated. The residue was then partitioned between 2N $Na_2CO_3$ and EtOAc. The dried extracts were evaporated to give a brown solid (166 mg).

T.l.c. ($SiO_2$) EtOAc:cyclohexane; 1:1, Rf 0.36

INTERMEDIATE 17

(5-Chloro-2,3,7,8-tetrahydro-1H-furo[2,3-g]indol-1-yl)-acetonitrile

A stirred solution of Intermediate 16 (165 mg), iodoacetonitrile (0.073 ml) and potassium carbonate (140 mg) in methyl isobutyl ketone (10 ml) was heated to reflux for 18 h under $N_2$. The mixture was cooled, and partitioned between 2N $Na_2CO_3$ and EtOAc. The dried extracts were evaporated to give a dark residue which was chromatographed on silica gel. Elution with $CH_2Cl_2$:EtOH:$NH_3$; 400:8:1 gave a pale brown solid (155 mg).

T.l.c. ($SiO_2$) $CH_2Cl_2$:EtOH:$NH_3$; 400:8:1, Rf 0.67

INTERMEDIATE 18

2-(5-Chloro-2,3,7,8-tetrahydro-1H-furo[2,3-g]indol-1-yl)-ethylamine

A mixture of Intermediate 17 (150 mg) in dry THF (5 ml) containing borane THF (1M in THF, 1.9 ml) was heated to reflux, under $N_2$, for 18 h. The mixture was cooled, and methanol (2 ml) added dropwise. 2N HCl (4 ml) was then added, and the mixture heated to reflux for a further 1 h. After cooling, the mixture was partitioned between saturated $K_2CO_3$ and EtOAc. The dried extracts were evaporated, and the red crystalline solid chromatographed on silica gel. Elution with $CH_2Cl_2$:EtOH:$NH_3$; 100:8:1 gave a pink crystalline solid (110 mg).

T.l.c. ($SiO_2$) $CH_2Cl_2$:EtOH:$NH_3$; 100:8:1, Rf 0.44

INTERMEDIATE 19

Cyclopropanecarboxylic acid (cyclopropanecarbonyl)-[2-(2,3 7,8-tetrahydro-1H-furo[2,3-g]indol-1-yl)-ethyl]-amide To a cold (0° C.) stirred solution of Intermediate 7 (111 mg) in $CH_2Cl_2$ (10 ml) and diisopropylethylamine (0.14 ml) was added cycloprepyl carbonyl chloride (0.074 ml) dropwise under $N_2$. The cooling bath was removed and the mixture stirred at 20° C. for 18 h. The mixture was partitioned between 2N $Na_2CO_3$ and EtOAc. The dried extracts were evaporated and the residue chromatographed on silica gel. Elution with EtOAc:cyclohexane; 1:4 gave a colourless oil (141 mg) which slowly crystallised.

T.l.c. ($SiO_2$) $CH_2Cl_2$:EtOH:$NH_3$; 200:8:1, Rf0.86

INTERMEDIATE 20

(2,2-Diethoxy-ethyl)-(2,3-dihydro-benzofuran-4-yl)-amine

A mixture of 2,3-dihydro-benzofuran-4-ylamine (preparation. *J. Hetereocyclic Chem.*, 18, 1333 (1980)) (4.34 g), potassium carbonate (8.87 g) and bromo acetaldehyde diethyl acetal (9.7 ml) in dry DMF (60 ml) was heated to 100° C. for 2 days under. The mixture was cooled and was partitioned between water and ethyl acetate. The dried extracts were evaporated and the residue chromatographed on silica gel (250 g). Elution with ethyl acetate:cyclohexane 1:4 gave the title compound as a pale yellow oil (4.95 g).

T.l.c. EtOAc:cyclohexane 1:1, Rf 0.73.

Analysis Found: C,66.8; H,8.5; N,5.35;

$C_{14}H_{21}NO_3$ requires: C,66.9; H,8.4; N,5.55%

INTERMEDIATE 21

N 2,2-Diethoxy-ethyl-N-2,3-dihydro-benzofuran-4-yl)-2,2,2-trifluoro-acetamide

Trifluoroacetic anhydride (4.12 ml) was added dropwise to a cooled (0° C.) stirring solution of the Intermediate 20 (6.67 g) and triethylamine (4.06 ml) in dichloromethane (100 ml) under nitrogen. The mixture was warmed to room temperature and stirred for 1½ h. The reaction mixture was partitioned between water and dichloromethane. The aqueous phase was re-extracted with dichloromethane. The combined organic layers were dried, evaporated and chromatographed on silica gel eluting with ethyl acetate:cyclohexane 1:9 gave the title compound (8.31 g) as a yellow oil.

T.l.c. Cyclohexane: EtOAc (4:1), Rf 0.38.

Analysis Found: C,55.30; H,5.74; N,3.96;

$C_{16}H_{20}F_3NO_4$ requires: C,55.33; H,5.8; N,4.03%

INTERMEDIATE 22

7,8-Dihydro-1H-furo[2,3-g]indole

A solution of the Intermediate 21 (8.27 g) in dichloromethane (80 ml) was added dropwise to a stirred solution of trifluoroacetic acid (80 ml) and trifluoroacetic anhydride (53 ml) in dichloromethane (800 ml) at 0° C. under nitrogen. This was warmed to room temperature and stirred for 20 h. The cooled reaction mixture was basified with 2N sodium hydroxide and then stirred for 1½ h at room temperature. The organic phase was separated and the aqueous layer was re-extracted with dichloromethane. The combined organic phases were dried, evaporated and chromatographed on silica gel eluting with EtOAc:Cyclohexane (1:9) gave the title compound as a beige solid (2.6 g).

T.l.c. cyclohexane: ethyl acetate 7:3, Rf 0.43.

Analysis Found: C,75.31; H,5.65; N,8.62;

$C_{10}H_9NO$ requires: C,75.45; H,5.70; N,8.80%

EXAMPLE 1

N-[2-(2,3,8,9-Tetrahydro-7H -pyrano[2,3-g]indol-1-yl)-ethyl]-acetamide

Acetic anhydride (0.104 ml) was added to a solution of the Intermediate 13 (160 mg) and pyridine (0.12 ml) in dry THF (4 ml) at 0° C. under $N_2$. The mixture was allowed to warm to room temperature and stirred for 3 h. The solvent was evaporated and the residue purified by flash column chromatography on silica. Elution with ethyl acetate gave the title compound as colourless crystals (151 mg), m.p. 91°–93° C.

T.l.c. Ethyl acetate, Rf 0.2.

EXAMPLE 2

N-[2-(2,3,8,9-Tetrahydro-7H-pyrano[2,3-g]indol-1-yl)-ethyl]-acetamide hydrochloride Ethereal HCl (0.25 ml) was added dropwise to a solution of the title compound of Example 1 (56 mg) in ethanol (2 ml) at 0° C. under $N_2$. The solvent was evaporated and the residue triturated under ether (2×1 ml). The solvent was decanted to give the title compound as a colourless solid (63 mg), m.p. 179°–181° C.

Analysis Found: C,58.6; H,7.5; N,8.95;

$C_{15}H_{20}N_2O_2$.HCl requires: C,58.6; H,7.3; N,9.1%

$^1$H N.m.r. ($CD_3OD$; δ) 7.2δ (1H,d), 6.9δ (1H, d), 4.24δ (2H,t), 4.07δ (2H,t), 3.6δ (4H,AA'BB'), 3.28δ (2H,t), 2.88δ (2H,t), 2.1–1.95δ (5H,m+s)

EXAMPLE 3

N-[2-(2,3,7,8-Tetrahydro-1H-furo[2,3-g]indol-1-yl)ethyl]-acetamide

To a stirred solution of Intermediate 7 (77 mg) in dry THF (5 ml) containing pyridine (0.09 ml) was added acetic anhydride (0.06 ml). After 18 h at 20° C. the mixture was partitioned between 2N $Na_2CO_3$ (30 ml) and EtOAc (2×30 ml). The dried extracts were evaporated and the residue chromatographed on silica gel (20 g). Elution with System A (200:8:1) gave the title compound as a colourless crystalline solid (56 mg), m.p. 126°–7° C.

T.l.c. System A (100:8:1) Rf0.42.

EXAMPLE 4

N-[2-(2,3,7,8-Tetrahydro-1H-furo[2,3-g]indol-1-yl)-ethyl]-acetamide hydrochloride The title compound of Example 3 (334 mg) was dissolved in ethyl acetate (20 ml) and was treated with ethereal HCl (1.35 ml). This was stirred at room temperature for 2 h and then the solvent was evaporated to give the title compound as a pale green powder (383 mg), m.p. 152°–154° C.

T.l.c. System A 100:8:1, Rf0.41.

Analysis Found: C,59.45; H,7.15; N,9.55; Cl,12.8;

$C_{14}H_{18}N_2O_2$.HCl requires: C,59.45; H,6.75; N,9.9; Cl,12.55%

EXAMPLE 5

N-[2-(5-Chloro-2,3,7,8-tetrahydro-1H-furo[2,3-g]indol-1-yl)-ethyl]-acetamide A solution of Intermediate 18 (107 mg) in dry THF (5 ml) and dry pyridine (0.11 ml) was treated with acetic anhydride (0.085 ml) and left for 2 days at 20° C. under $N_2$. The mixture was partitioned between 2N $Na_2CO_3$ and EtOAc. The dried extracts were evaporated, and the residue chromatographed on silica gel. Elution with $CH_2Cl_2$:EtOH:$NH_3$; 200:8:1 gave the title compound as a colourless crystalline solid (114 mg), m.p. 147°–9° C.

Assay Found: C,60.15; H,6.35; N,10.05;

$C_{14}H_{17}ClN_2O_2$ requires: C,59.9; H,6.1; N,10.0%

T.l.c. ($SiO_2$) $CH_2Cl_2$:EtOH:$NH_3$; 100:8:1, Rf 0.69

EXAMPLE 6

Cyclopropanecarboxylic acid [2-(2,3,7,8-tetrahydro-1H-furo[2,3-g]indol-1-yl)-ethyl]-amide Intermediate 19 (140 mg) was stirred in methanol (10 ml) and 2N NaOH (4 ml) at 20° C. under $N_2$ for 18 h, and then at reflux for 1 h. The mixture was diluted with water and extracted with EtOAc. The dried extracts were evaporated giving the title compound as a colourless solid (111 mg), m.p. 147°–9° C.

Assay Found: C,70.9; H,7.45; N,10.15;

$C_{16}H_{20}N_2O_2$ requires: C,70.55; H,7.4; N,10.3%

T.l.c. ($SiO_2$) $CH_2Cl_2$:EtOH:$NH_3$; 200:8:1, Rf 0.48

EXAMPLE 7

N-[2-(2,3,7,8-Tetrahydro-1H-furo[2,3-g]indol-1-yl)-ethyl]-acetamide

A mixture of Intermediate 4 (50 mg), potassium iodide (1 g) and N-(2-chloroethyl)acetamide (96 mg) in acetone (5 ml) was heated to reflux for 2 days. The cooled mixture was partitioned between water and ethyl acetate. The extracts were dried, and evaporated, and the residue chromatographed on silica gel. Elution with $CH_2Cl_2$:EtOH:$NH_3$; 400:8:1 gave a sample of desired material (69 mg).

T.l.c. ($SiO_2$) System A; 100:8:1, Rf 0.42

$^1$H n.m.r. agrees with assignment for alternative mutes of preparation.

6.85δ (1H,d), 6.2δ (1H,d), 5.86δ (1H,brs), 4.52δ (2H,t), 3.5–3.3δ (6H,m), 3.22δ (2H,t), 2.93δ (2H,t), 2.0δ (3H,s)

EXAMPLE 8

Compounds of formula (I) have been shown to exhibit high affinity and selectivity for binding to melatonin receptors in chicken retinal membranes, measured according to the methods of Dubocovich and Takahashi (Proc. Natl. Acad. Sci. (1988), 84, 3916–3820). The compounds of formula (I) have either melatonin agonist or antagonist activity as demonstrated in rabbit retina, according to the methods of Dubocovich (J. Pharmacol. Exp. Therap. (1985), 234, 395–401). The results obtained for particular compounds according to the present invention are as follows:

| Compound | Chicken retina Ki (nM) | Rabbit retina $IC_{50}$ (nM) |
| --- | --- | --- |
| Example 2 | 4.92 | 0.950 |
| Example 3 | 0.42 | 0.040 |
| Example 5 | 3.21 | 0.004 |
| Example 6 | 1.68 | 0.200 |

EXAMPLE 9

Compounds of formula (I) have been included in pharmacy formulations, and details of such formulations are given below.

TABLETS FOR ORAL ADMINISTRATION

A. Direct Compression

|  | mg/tablet |
|---|---|
| Active ingredient | 49.0 |
| Anhydrous Lactose | 55.2 |
| Microcrystalline cellulose | 37.5 |
| Pregelatinised maize starch | 7.5 |
| Magnesium stearate | 0.8 |

The active ingredient was sieved and blended with the excipients. The resultant mix was compressed into tablets using a tablet machine fitted with appropriately sized concave punches.

B. Wet Granulation

|  | mg/tablet |
|---|---|
| Active ingredient | 7.0 |
| Lactose BP | 146.5 |
| Starch BP | 30.0 |
| Pregelatinised Maize Starch BP | 15.0 |
| Magnesium Stearate BP | 1.5 |
| Compression weight | 200.0 |

The active ingredient was sieved through a suitable sieve and blended with lactose, starch and pregelatinised maize starch. Suitable volumes of purified water were added and the powders were granulated. After drying, the granules were screened and blended with the magnesium stearate. The granules were then compressed into tablets using suitable diameter punches.

Tablets of other strengths may be prepared by for example altering the ratio of active ingredient to lactose or the compression weight and using punches to suit.

|  | Unit formula (mg/tablet) |
|---|---|
| Active ingredient/lactose granule* | 93.0 |
| Microcrystalline cellulose Ph Eur | 5.5 |
| Croscarmellose Sodium USNF | 1.0 |
| Magnesium Stearate Ph Eur | 0.5 |
| *Active ingredient/lactose granule | mg |
| Active ingredient | 140.0 |
| Lactose Ph Eur 170 mesh | 140.0 |
| Purified water Ph Eur | qs + |

+ The water does not appear in the final product. Typical range 100–140 g per kg of blend.

The active ingredient and lactose were mixed together and granulated by the addition of purified water. The granules obtained after mixing were dried and passed through a screen, and the resulting granules were then mixed with the other tablet core excipients. The mix is compressed into tablets.

The tablets may be film coated with suitable film-forming materials, such as hydroxypropyl methylcellulose, using standard techniques. Alternatively the tablets may be sugar coated, or enteric coated.

| Coating Suspension | % w/w |
|---|---|
| Hydroxypropyl methylcellulose Ph Eur | 10.0 |
| Opaspray white# | 5.0 |
| Purified water Ph Eur to | 100.0++ |

++The water does not appear in the final product. The maximum theoretical weight of solids applied during coating is 11 mg/tablet.
Opaspray white is a proprietary film coating suspension, obtainable from Colorcon Ltd, UK, which contains hydroxypropyl methylcellulose and titanium dioxide.

The tablets were film coated using the coating suspension in conventional film coating equipment.

EFFERVESCENT TABLET

|  | mg/tablet |
|---|---|
| Active ingredient | 140.0 mg |
| Sodium bicarbonate | 656.4 mg |
| Monosodium citrate anhydrous | 659.5 mg |
| Aspartame | 40.0 mg |
| Polyvinylpyrrolidone | 32.0 mg |
| Sodium benzoate | 48.0 mg |
| Orange flavour | 16.0 mg |
| Lemon flavour | 8.0 mg |
| Absolute alcohol for granulation |  |

The active ingredient, anhydrous monosodium citrate, sodium bicarbonate and aspartame were mixed together and granulated by the addition of a solution of the polyvinylpyrrolidone in the alcohol. The granules obtained after mixing were dried and passed through a screen, and the resulting granules were then mixed with the sodium benzoate and flavourings. The granulated material was compressed into tablets using a machine fitted with 20 mm punches.

A rotary machine fitted with 20 mm punches may also be used for tabletting.

LIQUID AND CAPSULE FORMULATIONS FOR ORAL ADMINISTRATION

Liquid formulations were prepared by slow addition of active ingredient into the other ingredients at 35°–50° C. with constant mixing (amounts are given as percentage w/w).

| Example | A | B |
|---|---|---|
| Active ingredient | 18.2 | 18.2 |
| Oleic acid | 60.985 | 68.485 |
| Polyethylene glycol 600 | 7.3 | 7.3 |
| Propylene glycol | 6.0 | 6.0 |
| Polysorbate 80 | 7.5 | — |
| Ascorbyl palmitate | 0.015 | 0.015 |

The liquid formulations were filled into hard gelatin capsules, each capsule containing 25 mg of active ingredient.

CAPSULES

|  | mg/capsule |
|---|---|
| Active ingredient | 49.0 |
| *Starch 1500 | 150.0 |
| Magnesium Stearate BP | 1.0 |
| Fill weight | 200.0 |

*A form of directly compressible starch.

The active ingredient was sieved and blended with the excipients. The mix was filled into size No. 2 hard gelatin capsules using suitable machinery. Other doses may be prepared by altering the fill weight and if necessary changing the capsule size to suit.

SYRUP

| Sucrose Free Presentation | mg/5 ml dose |
|---|---|
| Active ingredient | 49.0 |
| Hydroxypropylmethylcellulose USP (viscosity type 4000) | 22.5 |
| Buffer | as required |
| Flavour | |
| Colour | |
| Preservative | |
| Sweetener | |
| Purified water BP to | 5.0 ml |

The hydroxypropylmethylcellulose was dispersed in hot water, cooled and then mixed with an aqueous solution containing the active ingredient and the other components of the formulation. The resultant solution was adjusted to volume and mixed. The syrup was clarified by filtration.

SUSPENSION

|  | mg/5 ml dose |
|---|---|
| Active ingredient | 49.0 |
| Aluminium monostearate | 75.0 |
| Sweetening agent | as required |
| Flavour | |
| Colour | |
| Fractionated coconut oil to | 5.0 ml |

The aluminium monostearate was dispersed in about 90% of the fractionated coconut oil. The resulting suspension was heated to 115° C. while stirring and then cooled. The sweetening agent, flavour and colour were added and the active ingredient was suitably dispersed. The suspension was made up to volume with the remaining fractionated coconut oil and mixed.

SUB-LINGUAL TABLET

|  | (mg/tablet) |
|---|---|
| Active ingredient/lactose granule* | 49.0 |
| Compressible sugar NF | 50.5 |
| Magnesium Stearate BP | 0.5 |
| Compression Weight | 100.0 |

The active ingredient was sieved through a suitable sieve, blended with the excipients and compressed using suitable punches. Tablets of other strengths may be prepared by altering either the ratio of active ingredient to excipients or the compression weight and using punches to suit.

SUPPOSITORY FOR RECTAL ADMINISTRATION

| Active ingredient | 49.0 mg |
|---|---|
| *Witepsol W32 | 1.0 g |

*A proprietary grade of Adeps Solidus Ph Eur

A suspension of the active ingredient in molten Witepsol was prepared and filled using suitable machinery, into 1 g size suppository moulds.

INJECTION FOR SUBCUTANEOUS ADMINISTRATION

|  | mg/ml |
|---|---|
| Active ingredient | 0.896 |
| Sodium Chloride Intravenous Infusion, BP, 0.9% w/v | to 1 ml |
| Batch size | 2500 ml |

The active ingredient was dissolved in a portion of the Sodium Chloride Intravenous Infusion, the solution made to volume with the Sodium Chloride Intravenous Infusion, and the solution thoroughly mixed. The solution was filled into clear, Type 1, glass 1 ml ampoules and sealed by fusion of the glass under a nitrogen or air headspace. The ampoules were sterilised by autoclaving at 121° C. for not less than 15 minutes. Alternatively the solution may be sterilised by filtration prior to filling aseptically into ampoules.

FOR INHALATION

Inhalation Cartridges

|  | mg/cartridge |
|---|---|
| Active ingredient (micronised) | 0.56 |
| Lactose BP | 25.00 |

The active ingredient was micronised in a fluid energy mill to a fine particle size range prior to blending with normal tabletting grade lactose in a high energy mixer. The powder blend was filled into No 3 hard gelatin capsules on a suitable encapsulating machine. The contents of the cartridges were administered using a powder inhaler such as the Glaxo Rotahaler.

Metered Dose Pressurised Aerosol

| Suspension Aerosol | mg/metered dose | Per can |
|---|---|---|
| Active ingredient (micronised) | 0.280 | 73.92 mg |
| Oleic Acid BP | 0.020 | 5.28 mg |
| Trichlorofluoromethane BP | 23.64 | 5.67 g |
| Dichlorodifluoromethane BP | 61.25 | 14.70 g |

The active ingredient was micronised in a fluid energy mill to a fine particle size range. The oleic acid was mixed with the trichloromethane at a temperature of 10°–15° C.

and the micronised drug was mixed into the solution with a high shear mixer. The suspension was metered into aluminium aerosol cans and suitable metering valves, delivering 85 mg of suspension, were crimped onto the cans and the dichlorodifluoromethane was pressure filled into the cans through the valves.

NASAL SPRAY

|  | % w/v |
|---|---|
| Active ingredient | 7.0 |
| Sodium Chloride BP | 0.9 |
| Purified Water BP to | 100 |
| Shot Weight | 100 mg (equivalent to 7 mg active ingredient) |

The active ingredient and sodium chloride were dissolved in a portion of the water, the solution made to volume with the water and the solution thoroughly mixed.

The pH may be adjusted to facilitate solution of the active ingredient, using acid or alkali and/or subsequently adjusted ideally to near neutrality taking into account the pH for optimum stability. Alternatively, suitable buffer salts may be used. The solution may be preserved with, for example, benzalkanium chloride and phenylethyl alcohol, for a multi-dose nasal spray.

We claim:

1. A compound of formula (I)

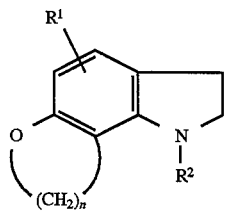

(I)

wherein $R^1$ is hydrogen, halogen or $C_{1-6}$ alkyl;

$R^2$ is a group of formula —$CR^3R^4(CH_2)_pNR^5COR^6$;

$R^3$, $R^4$ and $R^5$, which may be the same or different, are hydrogen or $C_{1-6}$ alkyl;

$R^6$ is $C_{1-6}$ alkyl or $C_{3-7}$ cycloalkyl;

n is an integer of 2, 3 or 4;

p is an integer of 1, 2, 3 or 4;

and pharmaceutically acceptable salts and solvates thereof.

2. A compound of formula (Ia)

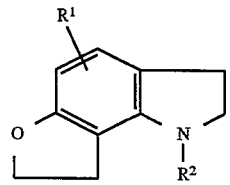

(Ia)

wherein, $R^1$ is hydrogen, halogen or $C_{1-6}$ alkyl;

$R^2$ is a group of formula —$CR^3R^4(CH_2)_pNR^5COR^6$;

$R^3$, $R^4$ and $R^5$, which may be the same or different, are hydrogen or $C_{1-6}$ alkyl;

$R^6$ is $C_{1-6}$ alkyl or $C_{3-7}$ cycloalkyl;

p is an integer of 1, 2, 3 or 4;

and pharmaceutically acceptable salts and solvates thereof.

3. A compound according to claim 1, wherein $R^2$ represents a group —$CR^3R^4(CH_2)_pNHCOR^6$ wherein $R^3$ and $R^4$ each independently represent hydrogen or $C_{1-3}$ alkyl, p is an integer of 1 or 2, and $R^6$ is $C_{1-3}$ alkyl or $C_{3-5}$ cycloalkyl.

4. A compound according to claim 1, wherein $R^1$ is selected from the group consisting of hydrogen, chlorine and $C_{1-3}$ alkyl.

5. N-[2-(2,3,8,9-Tetrahydro-7H-pyrano[2,3-g]indol-1-yl) -ethyl]-acetamide;

N-[2-(5-Chloro-2,3,7,8-tetrahydro-1H-furo[2,3-g]indol-1-yl)-ethyl]-acetamide;

Cyclopropanecarboxylic acid [2-(2,3,7,8-tetrahydro-1H-furo[2,3-g]indol-1-yl)-ethyl]-amide;

and pharmaceutically acceptable salts and solvates thereof.

6. N-[2-(2,3,7,8-Tetrahydro-1H-furo[2,3-g]indol-1-yl)-ethyl]-acetamide and pharmaceutically acceptable salts and solvates thereof.

7. A pharmaceutical formulation comprising a compound of formula (I) according to claim 1, together with one or more pharmaceutically acceptable carriers therefor.

8. A process of preparing a pharmaceutical formulation comprising a compound of formula (I) according to any of claim 1, together with one or more pharmaceutically acceptable carriers therefor, which process comprises mixing said compound of formula (I) together with said one or more pharmaceutically acceptable carriers therefor.

9. A compound of formula (I) according to claim 1, for use in therapy.

10. A compound of formula (I) according to claim 1, for use in the preparation of a medicament for use in the treatment of conditions associated with a disturbed functioning of the melatonin system.

11. A method of treating a mammal comprising administration of an effective amount of a compound of formula (I) according to claim 1, for the treatment of conditions associated with a disturbed functioning of the melatonin system.

12. A process of preparing a compound of formula (I) according to claim 1, which process comprises:

(a) acylation of a compound of formula (II)

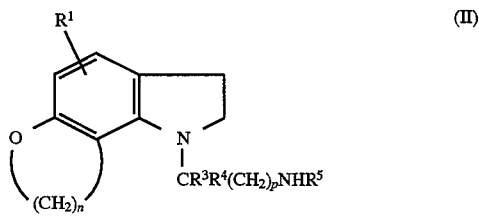

(II)

or (b) treating a compound of formula (XII)

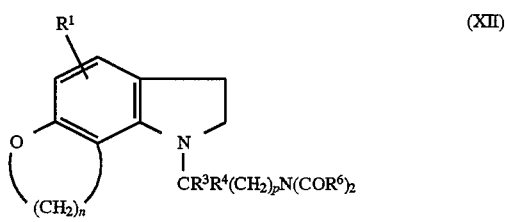

(XII)

with an alkali metal hydroxide;

or (c) alkylation of a compound of formula (IV)

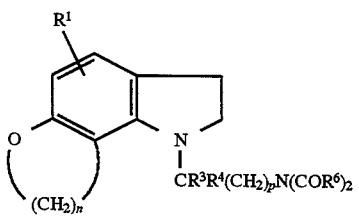
(IV)

13. A compound according to claim 2 wherein $R^2$ represents a group —$R^3R^4(CH_2)_p$NHCOR$^6$ wherein $R^3$ and $R^4$ each independently represent hydrogen or $C_{1-3}$ alkyl, p is an integer of 1 or 2, and $R^6$ is $C_{1-3}$ alkyl or $C_{3-5}$ cycloalkyl.

14. A compound according to claim 2 wherein $R^1$ is selected from the group consisting of hydrogen, chlorine and $C_{1-3}$ alkyl.

15. A compound according to claim 3 wherein $R^1$ is selected from the group consisting of hydrogen, chlorine and $C_{1-3}$ alkyl.

16. A pharmaceutical formulation comprising a compound of formula (Ia) according to claim 2, together with one or more pharmaceutically acceptable carriers therefor.

17. A method of treating a mammal, including man, comprising administration of an effective amount of a compound of formula (Ia) according to claim 2, for the treatment of conditions associated with a disturbed functioning of the melatonin system.

* * * * *